US 9,458,452 B2

United States Patent
Singer et al.

(10) Patent No.: US 9,458,452 B2
(45) Date of Patent: Oct. 4, 2016

(54) METHOD AND DEVICE FOR ISOLATING AND PURIFYING DOUBLE-STRANDED NUCLEIC ACIDS

(75) Inventors: Thorsten Singer, Solingen (DE); Holger Wedler, Hilden (DE)

(73) Assignee: QIAGEN GmbH, Hilden (DE)

(*) Notice: Subject to any disclaimer, the term of this patent is extended or adjusted under 35 U.S.C. 154(b) by 57 days.

(21) Appl. No.: 13/884,416

(22) PCT Filed: Nov. 8, 2011

(86) PCT No.: PCT/EP2011/069644
§ 371 (c)(1),
(2), (4) Date: May 9, 2013

(87) PCT Pub. No.: WO2012/062753
PCT Pub. Date: May 18, 2012

(65) Prior Publication Data
US 2013/0237699 A1    Sep. 12, 2013

(30) Foreign Application Priority Data

Nov. 9, 2010 (EP) .................................. 10014396

(51) Int. Cl.
| | |
|---|---|
| *C07H 21/00* | (2006.01) |
| *C12N 15/10* | (2006.01) |
| *B01D 15/34* | (2006.01) |
| *B01D 15/38* | (2006.01) |
| *C07H 1/08* | (2006.01) |

(52) U.S. Cl.
CPC .............. *C12N 15/101* (2013.01); *B01D 15/34* (2013.01); *B01D 15/3828* (2013.01); *C07H 1/08* (2013.01)

(58) Field of Classification Search
CPC ................................................... C12N 15/101

USPC .......................................................... 536/25.4
See application file for complete search history.

(56) References Cited

U.S. PATENT DOCUMENTS

| | | | |
|---|---|---|---|
| 6,383,393 B1 | 5/2002 | Colpan et al. | |
| 7,598,371 B2* | 10/2009 | Willson et al. | ............... 536/25.4 |
| 7,667,010 B2* | 2/2010 | Gierde et al. | ................. 530/412 |
| 8,062,533 B2* | 11/2011 | Dawson | ........................ 210/787 |

(Continued)

FOREIGN PATENT DOCUMENTS

| | | |
|---|---|---|
| DE | 43 21 904 A1 | 1/1995 |
| DE | 10 2007 005655 A1 | 8/2008 |

(Continued)

OTHER PUBLICATIONS

Balan, Sindhu et al., "Metal chelate affinity precipitation of RNA and purification of plasmid DNA," *Biotechnology Letters*, 25:1111-1116 (2003).

Forcic, Dubravko et al, "Purification of genomic DNA by short monolithic columns," *Journal of Chromatography A*, 1065:115-120 (2005).

(Continued)

*Primary Examiner* — Jezia Riley
(74) *Attorney, Agent, or Firm* — Seed IP Law Group PLLC

(57) ABSTRACT

The invention relates to a chromatographic device for isolating and/or purifying double-stranded nucleic acids, preferably double-stranded DNA, from a mixture of such nucleic acids with single-stranded nucleic acids, oligonucleotides, mononucleotides, salts and/or other such impurities. The invention also relates to a method for chromatographically isolating and/or purifying same, and to a kit for this purpose.

36 Claims, 8 Drawing Sheets

(56) References Cited

U.S. PATENT DOCUMENTS

2004/0152076 A1 8/2004 Willson et al.
2007/0275920 A1 11/2007 Muller et al.
2010/0048867 A1 2/2010 Mueller

FOREIGN PATENT DOCUMENTS

| EP | 1 559 783 A1 | 8/2005 |
| EP | 1 911 844 A1 | 4/2008 |
| WO | 99/00168 A1 | 1/1999 |
| WO | 01/38516 A1 | 5/2001 |
| WO | 02/46398 A2 | 6/2002 |
| WO | 2004/011142 A1 | 2/2004 |
| WO | 2012/062753 A1 | 5/2012 |

OTHER PUBLICATIONS

Ihara, Toshihiro et al., "DNA Separation Using Zr(IV)-Loaded Resin Through Ligand Exchange," *Analytical Sciences*, 17 Suppl. :IL229-IL231 (2001).
International Search Report for International Application No. PCT/EP2011/069644, mailed on May 2, 2013.
Min, Changhee et al., "Immobilized metal affinity chromatography of DNA," *Nucleic Acids Research*, 24(19):3806-3810 (1996).
Murphy, Jason C. et al., "Nucleic Acid Separations Utilizing Immobilized Metal Affinity Chromatography," *Biotechnology Progress*, 19:982-986 (2003).
Teeters, M.A. et al., "Adsorptive membrane chromatography for purification of plasmid DNA," *Journal of Chromatography A*, 989:165-173 (2003).

* cited by examiner

METHOD AND DEVICE FOR ISOLATING AND PURIFYING DOUBLE-STRANDED NUCLEIC ACIDS

The present invention relates to a chromatographic device for isolating and/or purifying double-stranded nucleic acids, preferably double-stranded DNA, to the use of said device for chromatographically isolating and/or purifying double-stranded nucleic acids, preferably double-stranded DNA, from a mixture of such nucleic acids with single-stranded nucleic acids and/or oligonucleotides, mononucleotides, salts and other contaminants, and to a method for chromatographically isolating and/or purifying double-stranded nucleic acids, preferably double-stranded DNA, from such a mixture and a kit therefor.

Since the discovery of the polymerase chain reaction (PCR), nucleic acids have gained huge importance in various areas in medicine and molecular biology and are used increasingly in, inter alia, recombinant gene technology, medical diagnostics, the development of new active ingredients, and forensics. PCR is, by now, among the most important methods in modern molecular biology and is used in medical and biological laboratories for, for example, identifying hereditary diseases and virus infections, in legal medicine for creating genetic fingerprints and for paternity tests, and also for cloning genes which, as a result of subsequent expression, can be used to produce proteins, for example as pharmacologically effective substances. The human genome project would also have been inconceivable without PCR.

PCR is a method which makes it possible to multiply (amplify) in vitro the genetic material deoxyribonucleic acid (DNA) using an enzyme, DNA polymerase. It is used in particular for amplifying a relatively short, precisely defined part of a DNA strand, with the products formed in this process themselves likewise being used as reactants in the following reaction cycle and an exponential amplification of the starting material thus being achieved. Owing to the exponential amplification of the starting material, even minute sample amounts suffice for sufficiently obtaining material for subsequent analyses, which generally require distinctly larger sample amounts. Nowadays, automating PCR makes it possible to amplify in parallel thousands of different DNA sequences within an extremely short time.

The PCR reaction mix contains, in addition to DNA containing the segment to be amplified (template), at least two different types of short oligonucleotide strands (primers), which define the starting point of DNA synthesis on both strands of the starting DNA, a DNA polymerase, and deoxyribonucleoside triphosphates (dNTPs), which serve as monomeric building blocks of the DNA strands synthesized by the DNA polymerase, and furthermore $Mg^{2+}$ ions as essential cofactors of the DNA polymerase and a buffer solution, which ensures the appropriate pH for the DNA polymerase in the reaction medium. After a completed reaction, the reaction mixture contains, in addition to the double-stranded deoxyribonucleic acids, excess mononucleotides, more particularly dNTPs, and primers, and also the enzyme, salts, further constituents of the buffer solution and possibly further contaminants. All these substances may have a disruptive effect in subsequent applications, for example sequencing reactions, by inhibiting them or causing artifacts. Especially in the field of molecular diagnostics, it is therefore vital to purify the reaction mixture obtained from PCR prior to further use in order to remove the aforementioned contaminants, such as excess dNTPs, primers, salts, etc.

Various methods for purifying PCR products are known from the prior art, more particularly for removing excess mononucleotides and primers and for desalting the sample. The double-stranded DNA (dsDNA) obtained as amplification product can, for example, be precipitated from the reaction mixture by addition of alcohols such as ethanol or isopropanol. However, such precipitation is not trivial especially in high-throughput methods, for example automated PCR in multiwell plates, owing to mixing operations and with regard to the subsequent separation of the alcohol from the precipitate. Furthermore, this method is limited with respect to the maximum PCR sample volume if the precipitation is to take place directly in the PCR reaction vessel, since a certain minimum volume of salt and alcohol must be added to the reaction mixture in order to achieve efficient precipitation. If the precipitation is not to take place in the reaction vessel, an additional step of transferring the PCR-obtained mixes is, on the other hand, necessary. In general, repeated, time-consuming centrifugation of the sample is further necessary in order to remove the precipitate, followed by a likewise time-consuming procedure for washing of the precipitated DNA, subsequent drying and resolubilization. Methods based thereon are thus virtually unautomatable, and furthermore the yields obtained are greatly dependent on the skill of the experimenter. In general, complete removal of the mononucleotides and primers is not achieved, and the residual salt content in the purified sample is also greatly dependent on the number of wash steps and the quality thereof.

For the processing of PCR-obtained samples for subsequent sequencing reactions, it is furthermore also possible to use the so-called ExoSAP method. For this purpose, the PCR-obtained reaction mixture is mixed with a mixture of two hydrolytic enzymes, viz. an exonuclease (I) and an alkaline phosphatase, for example shrimp alkaline phosphatase, in a suitable buffer. While exonuclease (I) degrades single-stranded primers and single-stranded DNA (ssDNA), the alkaline phosphatase dephosphorylates the remaining dNTPs. In a subsequent step, the sample must be treated at 80° C. for 15 minutes in order to denature the hydrolytic enzymes. Although this method is suitable for processing PCR-obtained reaction mixtures for the subsequent sequencing, the samples obtained in this manner are not suitable for a multiplicity of further reactions, since, firstly, salts present in the sample are not removed and the dephosphorylated nucleosides, inorganic phosphates and deactivated enzymes remain in the sample.

A further method for separating and concentrating high-molecular-weight substances from low-molecular-weight substances is ultrafiltration, in which a solution containing a mixture of low-molecular-weight substances (in the case of PCR: for example, salts, dNTPs, solvent and primers) and high-molecular-weight substances (for example, long-chain DNA) is pressed, by means of vacuum or positive pressure, against an ultrafiltration membrane composed of stainless steel, plastic or textile fabric having pores with a defined cut-off. Those substances which are larger than the membrane pores are in this case retained by the membrane, whereas substances which are smaller than the membrane pores can pass through the membrane. A disadvantage of this method is that the sample retentate remaining on the membrane must be redissolved or resuspended in a subsequent step and must be transferred by pipetting into suitable vessels for storage or further conversion. Furthermore, ultrafiltration is a purely physical separation method based on the difference in molecular size between the substance to be isolated and the contaminants. Therefore, it cannot be used, for example, for separating long-chain single-stranded nucleic acids, for example RNA, from double-stranded nucleic acids of a comparable size.

Other methods are based on the selective binding of the DNA to be isolated to a stationary phase, either by adsorption, absorption or covalent chemical bonding. In a first step, the DNA to be isolated is bound selectively to the stationary phase under appropriate conditions. The contaminants do not interact with the stationary phase to the same extent as the DNA to be isolated and can therefore be removed by appropriate wash steps. After removal of the contaminants, a further step for detaching the DNA from the stationary phase (desorption) is necessary, in which step the addition of suitable solvents minimizes the interaction between the DNA and the stationary phase. This "bind-wash-elute" principle is utilized by, for example, methods in which the DNA to be isolated is bound to silica particles under chaotropic conditions and/or in the presence of alcohols. In this case, a multiple of the original sample solution volume of chaotropic salt solution and/or alcohol must often be added to the sample before the DNA can be selectively bound to the silica particles. Multiple wash steps are necessary to remove the contaminants. In order to subsequently completely detach the DNA from the silica particles, the addition of a suitable low-salt buffer is necessary. The elution buffer volume required for this purpose frequently leads to a low concentration of the DNA in the sample obtained after purification, and so additional concentration steps are necessary. In some cases, the bound DNA cannot be completely removed from the particles even with appropriate volumes of the elution solution, and this leads to losses in yield. Especially in the field of high-throughput analysis, when using filter plates, there is furthermore frequently the introduction of ethanol from the wash buffer used into the purified samples, the removal of which makes an additional procedural step for ethanol evaporation necessary.

A further example of a method based on the so-called "bind-wash-elute" routine is anion-exchange chromatography (AEX). Anion-exchange methods are based on the interaction between the negatively charged phosphates of the nucleic acid and the positively charged surface of the anion-exchange material (Forcic et al. *J. Chromatogr.* A 2005, 1065(1), 115-120). Under low-salt conditions, the DNA present in a sample binds selectively to the stationary phase, while contaminants can be removed in subsequent wash steps by using wash buffers having a medium salt concentration. In a further step, the DNA can be eluted by desorption from the stationary phase using a high-salt buffer. Owing to the high salt content of the elution buffer, precipitation of the DNA from the eluate using alcohol is subsequently necessary.

Although methods based on the selective binding of DNA generally provide DNA of high purity, multiple procedural steps for the binding, washing and elution of the DNA are always necessary here, and this can sometimes be time-consuming and cost-intensive.

Furthermore, there have already been attempts in the prior art to overcome at least some of the respective disadvantages of the particular methods by combining at least two different methods of the abovementioned methods.

Firstly, there is of course the option of implementing two or more of the abovementioned methods in succession in separate devices. However, for reasons of time and cost, this procedure is only practical in those cases in which only particular specific samples are to be obtained in a highly pure form, but certainly not in high-throughput analyses.

Therefore, there have also been isolated attempts to combine two or more of the abovementioned methods in one device.

For example, WO 99/00168 describes a device for purifying biological molecules, in which device an adsorptive chromatography medium is combined with a size-exclusion chromatography medium. The adsorptive medium is, for example, an ion-exchange chromatography resin. In a first step, the biological molecule to be isolated and/or to be purified is bound to this medium under the above-described conditions. As a result of one or more wash steps, the contaminants, which do not interact with the chromatography medium to the same extent as the molecule to be isolated, are then separated therefrom by washing. Lastly, a suitable elution buffer desorbs the desired molecule from the adsorptive medium. In contrast to the abovementioned methods, the method described in WO 99/00168 is notable for the fact that the adsorptive medium is combined with a subsequent size-exclusion chromatography medium. As a result, low-molecular-weight components can be removed from the mobile phase under appropriate conditions. If the volume of the desorptive elution buffer is precisely controlled, the molecule to be isolated can be obtained in a desalted eluate and an additional step for precipitating the biological molecule is omitted, which step is a disadvantage of conventional ion-exchange chromatography. Nevertheless, this method is also still comparatively time-consuming, since at least three steps for the binding, washing and desorptive elution of the desired molecule must be carried out. Furthermore, the molecule to be isolated must be distinctly larger than the contaminants, so that it can pass rapidly enough through the size-exclusion chromatography medium in the desorptive elution step without smaller molecules, which have already entered into the pores of the size-exclusion chromatography medium during the attachment of the target molecule to the adsorptive phase or during washing, being eluted together with the target molecule in the desorptive elution step.

In addition, WO 2004/011142 describes so-called SEIE particles, which are likewise said to combine the advantages of size exclusion chromatography with the advantages of ion-exchange chromatography. Here, preference is given to particles in which a core composed of an ion-exchange chromatography medium (IEX medium) is enclosed in a shell composed of a size-exclusion chromatography medium (SEC medium). Small molecules such as inorganic ions and dNTPs can pass through the size-exclusion shell and are retained in the core of the particles by the ion-exchange medium, whereas larger molecules, such as long single-stranded nucleic acids or double-stranded nucleic acids, are too large to penetrate the pores of the size exclusion medium and therefore remain in solution. Although the devices mentioned in WO 2004/011142 are suitable for removing mononucleotides (dNTPs), short oligonucleotide primers, salts and metal ions from a biological sample, it is not possible with this method to remove contaminants which are comparable to the double-stranded nucleic acids to be isolated in terms of their size or their hydrodynamic radius. Finally, separation is based mainly on molecular size.

Thus, all the methods known from the prior art for purifying DNA, more particularly for purifying PCR products, generally comprise multiple procedural steps, and this alone makes these methods time-consuming. Furthermore, the known methods are in some cases very labor-intensive and cost-intensive and error-prone. Particularly for high-throughput methods, there is furthermore a requirement for automation-specific instruments, whose production and maintenance costs greatly increase with the number of different steps to be carried out thereby. Therefore, none of the steps known to date meets all the requirements for rapid and reproducible purification of double-stranded nucleic acids, more particularly PCR products, which purification provides products of high quality coupled with high reproducibility.

It is therefore an object of the present invention to provide a device and a method which allows the isolation and/or purification of double-stranded nucleic acids, more particularly double-stranded DNA obtained as PCR amplification products, in a single procedural step and reliably removes both single-stranded nucleic acids, for example oligonucleotides used as primers, mononucleotides, more particularly dNTPs, and salts in a single reaction step without subsequent steps for resolubilization or resuspension of the DNA, for transfer of the purified sample or for concentration being necessary.

It has now been found that, surprisingly, this can be achieved using a chromatographic device for isolating and/or purifying double-stranded nucleic acids, preferably double-stranded DNA, comprising: (1) a base body, (2) at least one cavity within the base body, which cavity is provided with an inlet and an outlet and (3) a stationary phase situated in the cavity, wherein the stationary phase comprises at the least at least one porous chromatography resin, which acts as a size-exclusion chromatography medium, and immobilized metal ions.

In contrast to the devices and methods known from the prior art for isolating and/or purifying double-stranded DNA, for example for isolating the amplification products of a PCR from the reaction mixture, the device according to the invention and the method according to the invention are notable for a range of advantages, as illustrated by table 1 below.

to the invention and the method according to the invention are notable for the fact that dsDNA can be obtained within a very short time (5 to 10 minutes) in a quantitative yield and very good quality in only two to three procedural steps, with the preparatory step of so-called "prespinning", when using a so-called spin column, for removing excess solvent from the stationary phase prior to application of the sample to the same stationary phase already being included in the calculation. As an additional solution, only a buffer solution for pH adjustment is required.

The device according to the invention allows the chromatographic isolation and/or purification of double-stranded nucleic acids by removal of contaminants and further sample constituents such as single-stranded nucleic acids, mononucleotides, more particularly dNTPs, nucleosides and salts in a single chromatographic step, by combining two purification principles in one stationary phase.

In the context of the invention, double-stranded nucleic acids are understood to mean double-stranded DNA as well as double-stranded hybrids composed of DNA and RNA and double-stranded RNA of any chain length, more particularly also plasmid DNA (pDNA), genomic DNA (gDNA) or fragments thereof. Preferably, the double-stranded nucleic acids are double-stranded DNA obtained as a PCR amplification product.

In the context of the invention, the stationary phase is understood to mean the entirety of the chromatography media present within the chromatographic device, comprising one or more chromatography media and immobilized metal ions, irrespective of whether a single chromatography medium, a homogeneous mixture of multiple chromatography media or an arrangement of multiple chromatography media in multiple layers is concerned.

TABLE 1

| | Alcohol precipitation | ExoSAP | MinElute spin | MinElute vacuum | QIAquick spin | QIAquick vacuum | QIAquick 96 vacuum | MinElute 96 UF | Present invention |
|---|---|---|---|---|---|---|---|---|---|
| Number of required steps | | | | | | | | | |
| Pipetting | 2 to 3 | 3 to 4 | 4 | 4 | 4 | 4 | 4 | 3 | 0 to 1 |
| Mixing | 1 | 2 | 1 | 1 | 1 | 1 | 1 | 1 | 0 |
| Negative pressure/Vacuum | 1 | 1 | 0 | 3 | 0 | 3 | 3 | 1 | 0 |
| Centrifugation | 2 | 2 | 4[1] | 1 | 4[1] | 1 | 1 | 0 | 2[1] |
| Total steps | 6 to 7 | 8 to 9 | 9[1] | 9 | 9[1] | 9 | 9 | 5 | 2 to 3[1] |
| Incubation (min) | 0 | 2 × 15 | 1 | 1 | 1 | 1 | 1 | 0 | 1 |
| Number of buffers/other solutions per kit | 2 to 3 | 3 to 4 | 3 | 3 | 3 | 3 | 3 | 2 | 1 |
| Time required (min) | 20 to 45 | About 30 | 5 to 10 | 5 to 15 | 5 to 10 | 5 to 15 | 25 | 20 | 5 to 10 |
| Quality of dsDNA obtained | Low to medium | Medium to good | Very good | Good to very good | Very good | Good to very good | Good to very good | Good to very good | Very good |
| Yield | <=100% | <=100% | >80% | >80% | >80% | >80% | >80% | >90% | 100% |
| Main disadvantages | Long centrifugation | Long centrifugation | Low throughput | Transfer of ethanol and salt into the purified sample | Low throughput | Transfer of ethanol and salt into the purified sample | Transfer of ethanol and salt into the purified sample | Ends with pipetting | |

[1]So-called "prespinning" to remove excess solvent from the stationary phase prior to application of the sample to the stationary phase has already been included in the calculation.

The systems ExoSAP (from USB Corporation, Cleveland, Ohio, USA), MinElute spin, vacuum and 96 UF (Qiagen, Hilden, Germany) and QIAquick spin, vacuum and 96 vacuum (Qiagen, Hilden, Germany) are commercially available, and protocols for their use are available from the manufacturer. Standard protocols for alcohol precipitation are known to a person skilled in the art. In contrast to these devices or methods based on their use, the system according Single-stranded nucleic acids, for example single-stranded DNA in the form of excess PCR amplification primers, are selectively bound to the stationary phase as a result of interaction of the immobilized metal ions with the aromatic nitrogenous bases of the single strand and thus removed from the mobile phase which passes through the stationary phase during chromatographic purification. Mononucleotides, more particularly excess dNTPs, can also be removed from the mobile phase as a result of interactions with immobilized metal ions. Whereas single-stranded nucleic acids such as oligonucleotides, long ssDNA and RNA, and mononucleotides exhibit a strong interaction with the immobilized metal ions, this interaction is low in double-stranded nucleic acids, since such a double strand is formed by hydrogen bonds of the in each case complementary bases of the two individual strands; the bases consequently lie in the interior of the double strand and are thus shielded from the outside. Double-stranded nucleic acids are therefore not bound to the stationary phase, but remain in the mobile phase and pass through the chromatographic device therewith.

In addition to immobilized metal ions, the stationary phase of the chromatographic device according to the invention also comprises a porous chromatography resin which acts as a size-exclusion chromatography medium. Size-exclusion chromatography (SEC) is a chromatographic method which makes it possible to separate different molecules on the basis of their size or their hydrodynamic volume. If an organic solvent is used as the mobile phase, size-exclusion chromatography is also referred to as gel-permeation chromatography (GPC); when using an aqueous mobile phase (water, aqueous organic solvent or an aqueous buffer), it is referred to as gel-filtration chromatography. In size-exclusion chromatography, the stationary phase used is a matrix which forms a gel bed as a result of swelling in an appropriate solvent. The matrices frequently used are cross-linked silicates or cross-linked organic polymers, which form pores of a defined size in their interior upon swelling in an appropriate solvent owing to the crosslinking.

Whereas small molecules can enter into these pores and pass through the gel bed more slowly than the mobile phase, large molecules cannot do this and pass through the stationary phase with the solvent of the mobile phase, i.e., distinctly faster than those molecules which are retained in the interior of the pores. The size-exclusion limit of a size-exclusion chromatography medium indicates the molecular weight above which the molecules present in the mobile phase are too large to enter into the stationary phase. This size-exclusion limit is determined by the size of the pores within the gel matrix and can be adjusted by the degree of cross-linking of the gel. Nowadays, a multiplicity of stationary phases for size-exclusion chromatography with a varying degree of crosslinking (size-exclusion limits) is commercially available.

Furthermore, as a result of the combination of a size-exclusion chromatography medium with immobilized metal ions, metal ions, whose detachment from the stationary phase during traditional immobilized metal ion affinity chromatography (IMAC chromatography) is observed in some cases (so-called "leaching"), are immediately removed from the mobile phase and do not reach the eluate, where they could interfere with subsequent applications, since, for example, divalent metal cations can act as inhibitors in subsequent assays for detecting the isolated nucleic acids.

In order to retain the stationary phase within the chromatographic device, the chromatographic device preferably comprises at least one porous filter, one porous frit or a membrane which is arranged between the outlet of the cavity and the stationary phase and retains the stationary phase in the cavity. Here, the pore size of said filter, said frit or said membrane is larger than the double-stranded nucleic acids to be isolated and/or purified, and so they emerge from the outlet with the mobile phase after elution has been effected and are not retained by the membrane as in the case of ultrafiltration.

Preferably, the chromatographic device comprises at least one closure device for closing the inlet and/or the outlet of the cavity. If both the inlet and the outlet are provided with such a closure device, the closure device used to close the inlet and that used to close the outlet can be the same or different.

In a preferred embodiment, the closure device is a removable disposable closure device selected from the group consisting of peelable films, tear-off lids or closure ends which can be broken off from the chromatographic device by twisting along a predetermined breaking point, without being restricted thereto. Furthermore, the at least one closure device can be in the form of a reusable closure device, for example in the form of twist-off or screw caps, snap-on lids or stoppers, without being restricted thereto.

In a preferred embodiment, both the inlet and the outlet of the chromatographic device are each provided with a closure device and the cavity formed by the base body contains the stationary phase preswollen in a solvent selected from the group consisting of water, homogeneous mixtures of organic solvents with water and aqueous buffer solutions. In this preferred embodiment, the excess solvent is preferably immediately removed prior to the use of the chromatographic device for isolating and/or purifying double-stranded nucleic acids.

The chromatographic device is not restricted to a specific form, but rather any embodiment typically used for chromatographic devices can be used, provided it comprises at least one cavity within the base body, which cavity is provided with an inlet and an outlet, and into which cavity a stationary phase can be filled. For example, the chromatographic device can be selected from glass or plastic columns typically used for positive-pressure and negative-pressure chromatography, spin columns or else multiwell plates, without being restricted thereto. In general, chromatographic columns are used which have a circular cross-section and whose diameter in relation to their length is low. Such columns can, for example, be cylindrical or conical in form.

A preferred embodiment of a suitable chromatographic device is shown in FIG. 1: the chromatographic device comprises a base body (1) which defines, within its interior, a cavity which is provided with an inlet (2) and an outlet (3) and in which the stationary phase (4) is situated, and also a porous frit (5) which retains the stationary phase (4) in the cavity. The inlet (2) of the chromatographic device is provided with a closure device (6) in the form of a lid.

The chromatographic device according to the invention can additionally comprise at least one collection vessel for collecting the mobile phase (eluate) emerging from the outlet after elution has occurred. The form and size of the collection vessel depends expediently on the amount of mobile phase emerging from the chromatographic device and on the form and size of the chromatographic device. A multiplicity of suitable collection vessels from the prior art are known to a person skilled in the art. If the chromatographic device comprises, for example, exactly one stationary phase-filled cavity, for example in the form of a single spin column, it expediently also comprises only one collection vessel for collecting the eluate. By contrast, if the chromatographic device is in the form of multiple cavities arranged in parallel, each containing a stationary phase, for example in the form of a multiwell plate, it advantageously also comprises multiple collection vessels, preferably in the form of a multiwell plate. Furthermore, additional collection vessels can also be present, for example for collecting excess solvent during packing of the column.

In a preferred embodiment, the immobilized metal ions are divalent, trivalent and/or tetravalent metal cations or mixtures thereof, preferably selected from the group consisting of $Zn^{2+}$, $Co^{2+}$, $Cu^{2+}$, $Ni^{2+}$, $Fe^{2+}$, $Mn^{2+}$, $Al^{3+}$, $Co^{3+}$, $Ga^{3+}$ and $Zr^{4+}$ or a combination thereof. Particularly preferably, the immobilized metal ions comprise at least one divalent metal cation selected from the group consisting of $Zn^{2+}$, $Co^{2+}$, $Cu^{2+}$, $Ni^{2+}$, $Fe^{2+}$ and $Mn^{2+}$, optionally in combination with $Al^{3+}$ ions, and more particularly at least $Cu^{2+}$ ions, optionally in combination with $Al^{3+}$ ions. However, an embodiment having only divalent metal cations is also suitable for the invention, i.e., without the presence of trivalent or tetravalent ions. In this case, the above-mentioned divalent ions are also preferred, either alone or in a combination of two or more of the above-mentioned ions.

Preferably, the metal ions are immobilized on at least part of the stationary phase by means of at least one linker. For this purpose, particularly suitable are linkers of the general formula A-R—Z, where A is an anchor group for covalent bonding of the linker to at least part of the stationary phase, Z is a polydentate head group for chelating the metal ions, and R is a linear, branched or cyclic hydrocarbon chain which connects the anchor group A and the head group Z and which can be substituted or unsubstituted and in which one or more carbon atoms can be replaced by heteroatoms such as O, N, S, Se.

Suitable anchor groups for covalent bonding of the linker to the stationary phase comprise, for example, —OH, —$CO_2H$, —$NH_2$, derivatives thereof such as acid chlorides, esters, more particularly active esters, anhydrides, etc., and further groups, provided they can be reacted with the matrix of the stationary phase, for example sepharose or polyacrylamide, to form a covalent bond.

Group R is used in particular as a spacer between the anchor group and the chelating head group and is therefore not subject to any particular requirements with respect to its length or structure, provided it is stable under the conditions used for covalent bonding of the linker to the stationary phase, of the subsequent loading of the linker with the metal ions and of the chromatographic isolation and purification of double-stranded nucleic acids on said phase. R can, for example, be an alkanediyl group, an alkenediyl group, an alkynediyl group, an aryldiyl group, an alkaryldiyl group or an aralkanediyl group. In these groups, it is additionally possible for one or more carbon atoms to be replaced by heteroatoms, and R can, for example, also be a spacer based on PEG or PPG (—$(OCH_2CH_2)_nO$— and —$(OCH_2CH_2CH_2)_nO$—, respectively, where n is a positive integer).

Head group Z acts as a polydentate ligand for complexing the metal ions, i.e., the head group contains at least two functional groups having free electron pairs which can occupy at least two coordination sites of the metal ion to form coordinate bonds. In contrast to complexes having monodentate ligands which are not linked to one another, chelate complexes are notable for higher stability owing to the lower entropy decrease upon complex formation and to the increased probability of recombination after detachment of an electron pair from the coordination sphere of the central atom. Suitable head groups are therefore those groups which have at least two functional groups having free electron pairs. Said functional groups can be the same or different and are preferably selected from the group containing —$CO_2H$, —$CO_2R^1$, —$CO_2NH_2$, —$CONHR^1$, —$CONR^2R^3$, —$CR^1R^2R^3NR^1R^2$, —$SO_3H$, —$PO_3H_2$, —SH, —OH, —$NH_2$ and —$OR^1$, where $R^1$, $R^2$ and $R^3$ are each a suitable organic radical, where preferably each $R^1$, $R^2$ and $R^3$ can be independently selected from linear, cyclic (if permitted by the number of carbons), saturated or unsaturated and possibly substituted $C_1$, $C_2$, $C_3$, $C_4$, $C_5$, $C_6$, $C_7$, $C_8$, $C_9$ or $C_{10}$ hydrocarbon chains.

In a preferred embodiment, the linker is selected from the group consisting of iminodiacetic acid (IDA), nitrilotriacetic acid (NTA), N-carboxymethylated aspartic acid (CM-Asp) and tris(2-ethylaminoethyl)amine (TREN).

The use of immobilized metal ions for chromatographically purifying proteins having histidine motifs, more particularly proteins having hexahistidine sequences (6× His-tag), has been known since the seventies and is, by now, a widespread method for purifying recombinant proteins which is based on the selective interaction of the nitrogen atoms of the heteroaromatic imidazole side chain of the histidine with immobilized metal ions such as $Ni^{2+}$ or $Cu^{2+}$. By contrast, the potential use of immobilized metal affinity chromatography for purifying nucleic acids, whose bases likewise have heteroaromatic nitrogen atoms, has not been investigated for a long time. Initial attempts to purify DNA molecules which had been modified with a specific recognition sequence (so-called affinity label) composed of six successive 6-histaminylpurine residues, comparable to the 6× His-tag of proteins, have been described by Min et al. (C. Min et al. *Nucleic Acids Research* 1996, 24(19), 3806-3810). The disadvantage of this method is the use of an affinity label, which makes additional steps for the introduction and removal thereof necessary.

In addition, the use of a Zr(IV)-loaded phosphonate resin as an adsorption medium for the chromatographic purification of DNA in a bind-wash-elute routine has been described (T. Ihara et al. *Analytical Sciences* 2001, 17 (Suppl.), i1229-i1231). The general disadvantages of so-called bind-wash-elute methods, in particular the additional number of method steps, have already been explained.

Furthermore, the literature describes methods for selectively precipitating RNA in the presence of linear DNA and plasmid DNA using copper-loaded polymers in a saline solution (S. Balan et al. *Biotechnology Letters* 2003, 25, 1111-1116). However, this method requires additional steps for removing the precipitate and for desalting the DNA remaining in the supernatant.

The removal of RNA from lysates obtained by the lysis of *E. coli* bacteria has also been described (J. C. Murphy et al. *Biotechnol. Prog.* 2003, 19, 982-986). The authors further described that it is possible in principle to remove oligonucleotide primers and PCR products having base mismatches from PCR mixes. However, they constantly observed the binding of a certain fraction of the double-stranded PCR product to the stationary phase, and this invariably leads to losses in yield. Furthermore, the removal of excess mononucleotides, more particularly dNTPs, is also not described here, and so yet additional steps for purifying the PCR product are necessary before or after primer removal.

By contrast, the present invention allows the selective removal of single-stranded nucleic acids, comprising, inter alia, RNA and oligonucleotide primers, and the removal of excess mononucleotides in a single chromatographic step. Furthermore, further contaminants present in the sample, for example salts, can also be simultaneously removed in said one chromatographic step. The simultaneous removal of mononucleotides and single-stranded nucleic acids is achieved in the present invention by preferably using a combination of different immobilized metal ions, particularly preferably a combination of a soft or intermediate metal ion such as, for example, $Ni^{2+}$ or $Cu^{2+}$ with a relatively hard metal ion such as, for example, $Al^{3+}$ or $Fe^{3+}$. The fact that this can bring about efficient and very rapid purification of PCR products in a single chromatographic step is all the more surprising since, according to the prior art, it had to be assumed up to now that the use of hard metal ions leads to unspecific interactions of immobilized metal ions with the phosphate backbone of nucleic acids and, in this case, not only single-stranded nucleic acids and dNTPs, but also double-stranded nucleic acids, more particularly double-stranded DNA, are adsorbed and selective removal of single-stranded nucleic acids is thus no longer possible (WO 02/46398).

The porous chromatography resin is preferably a crosslinked silicate or a crosslinked organic polymer which, upon mixing with water, an aqueous solution or an aqueous buffer, forms a matrix having internal pores of a defined size (size-exclusion chromatography resin). Preferably, the porous chromatography resin is selected from the group containing dextrans, agarose, polyacrylamides, propylene carbonate and silicates or mixtures thereof, which, for example, are commercially available under the trade names Sephadex, Sephadex LH, Sepharose, Sephacryl, Superose, Superdex, Chromasolve, Chromasil and Nucleosil with various size-exclusion limits (degrees of crosslinking).

Preferably, the size-exclusion chromatography resin has a size-exclusion limit which allows small molecules such as, for example, salts or peptides below a molecular weight of $10^4$, preferably below $10^3$, more preferably below $10^2$, daltons (as globular proteins in each case) to enter into the pores, whereas larger molecules (above the aforementioned molecular weight) cannot enter into the pores and pass through the resin more quickly. Particularly double-stranded nucleic acid chains of more than 80, preferably more than 100, bp should be able to pass through the resin quickly without substantially entering into the pores. This can be easily determined by routine experiments using the commercially available resins. Particularly preferably, the invention uses a Sephadex material (for example, from Sigma-Aldrich).

Critical for efficient and rapid purification of double-stranded nucleic acids is the fact that the stationary phase comprises both internal pores for removing molecules having a low hydrodynamic radius and/or ions, for example dissolved salts, and immobilized metal ions for selectively binding single-stranded nucleic acids and mononucleotides. However, the specific arrangement of these two features within the stationary phase of the device according to the invention is not of critical importance to the success of chromatographic purification.

For instance, in a preferred embodiment of the device according to the invention, the stationary phase comprises, in addition to the at least one porous chromatography resin (size-exclusion chromatography resin), at least one further material on which the metal ions are immobilized. Here, the at least one further material can be any type of suitable support for the metal cations, selected from particulate supports such as, for example, beads, powders, granules, crystals or the like, membranes, sintered particles of any form and size or else frits, meshes, fibers or similar suitable supports. The at least one further material can, for example, be selected from large-pored zeolites, mordenites or similar, porous foams, porous resins, polymer beads, including meshed beads, surfaces of nonporous, monolithic structures such as, for example, inorganic monolithic structures which are used in catalytic reactions, or polymeric structures, for example epoxy resins, or else from mixtures of the aforementioned.

The material is preferably selected from customary chromatography resins, and the material on which the metal ions are immobilized can be the same as the size-exclusion chromatography resin or can differ therefrom, for example can be a different porous resin, or else a nonporous chromatography resin.

Preferably, the material used as support for the metal ions is selected from polymer resins known to be suitable for ligand functionalization, including Sepharose, chemically and/or physically modified Sepharose, agarose, chemically and/or physically modified agarose, other polymeric sugars or chemically and/or physically modified versions thereof, cellulose, chemically and/or physically modified cellulose, polyolefins, chemically and/or physically modified polyolefins, polydienes, chemically and/or physically modified polydienes, polyurethanes, chemically and/or physically modified polyurethanes, polypeptides, chemically and/or physically modified polypeptides, polyamides, chemically and/or physically modified polyamides, polyalkylene oxides, chemically and/or physically modified polyalkylene oxides such as, for example, polyethylene glycols, chemically and/or physically modified polyethylene glycols, silicones, elastomers, thermoplastics, thermoplastic elastomers or other polymeric substrates, without being restricted thereto.

Suitable membranes include permeable membranes or semipermeable membranes, chemically and/or physically modified membranes; suitable inorganic supports include silicas, silicates, aluminum oxides, silica-aluminum oxides, zeolites, mordenites, aluminates, clay earths, or any other type of suitable inorganic support; suitable metallic supports include gold, gold alloys, platinum, platinum alloys, silver, silver alloys, iron, iron alloys, for example any type of steel, copper, copper alloys such as, for example, brass or bronze, tin, tin alloys, aluminum, aluminum alloys, silicon, silicon alloys and other semiconductors, without being restricted thereto in each case.

If a combination of different metal ions is used, they can be immobilized together on exactly one further material or else can each be immobilized on different materials, which are arranged in individual layers or in mixtures.

In a preferred embodiment, the porous chromatography resin and the additional material exhibiting the metal ions in the chromatographic device are arranged substantially separately from one another, preferably in the form of two successive layers in the flow direction of the mobile phase from the inlet to the outlet, particularly preferably in such a way that the material on which the metal ions are immobilized is arranged as the upper layer and the size-exclusion chromatography resin is arranged as the lower layer. Such a preferred embodiment is, for example, shown diagrammatically in FIG. 2. Here, the layers follow one another directly, i.e., are in contact via at least one surface, and so the mobile phase, when emerging from one layer, immediately enters the other layer and transfer of the partially purified sample is not necessary, as would be required, for example, if immobilized metal ion chromatography were implemented before or after size-exclusion chromatography in two separate chromatographic devices.

Alternatively, the porous chromatography resin and the additional material in a further preferred embodiment in the chromatographic device according to the invention can be largely present as a homogeneous mixture (so-called mixed-bed resin). This embodiment is shown diagrammatically in FIG. 3.

In the two abovementioned embodiments, the material on which the metal ions are immobilized can either be the same as the chromatography resin used, or differ therefrom. In the latter case, one of the abovementioned materials which does not interact unspecifically with the nucleic acid to be purified is preferably used.

The embodiments according to FIGS. 2 and 3 are particularly preferred.

In a further possible preferred embodiment, the metal ions are themselves immobilized on the size-exclusion chromatography resin. In this case, further addition of unmodified chromatography resin is not necessary. This embodiment is shown diagrammatically in FIG. 4.

In addition, the stationary phase can also comprise both a porous chromatography resin and at least one additional material, with the metal ions being immobilized both on the porous chromatography resin and on the at least one additional material.

Particularly in one embodiment in which the porous chromatography resin also bears immobilized metal ions, it is particularly preferred for the chromatography resin to be selected from crosslinked silicates and/or crosslinked polymers selected from dextrans, agarose, polyacrylamides and propylene carbonates, or mixtures thereof, with preferably the pore size thereof being defined such that small molecules such as, for example, salts or peptides below a molecular weight of $10^4$, preferably below $10^3$, more preferably below $10^2$, daltons (as globular proteins in each case) can enter into the pores, whereas larger molecules (above the abovementioned molecular weight) cannot enter into the pores and pass through the resin more rapidly. Particularly double-stranded nucleic acid chains of more than 80, preferably more than 100, by should be able to pass through the resin quickly without substantially entering into the pores. Particularly preferred are dextrans, polyacrylamides, propylene carbonates and silicates or mixtures thereof.

In a preferred embodiment, the chromatographic device comprises exactly one stationary phase-filled cavity and is preferably in the form of a spin column. Particularly preferably, the device is designed such that it can be inserted into a customary reaction vessel (such as, for example, an Eppendorf tube) and the eluate can be collected in such a reaction vessel.

In a further preferred embodiment, the chromatographic device allows the parallel isolation and/or purification of double-stranded nucleic acids from different samples using a single device, with the chromatographic device comprising multiple cavities which are each filled with the stationary phase and which are arranged in parallel. In a preferred embodiment, such a device for the simultaneous isolation and/or purification of double-stranded nucleic acids from different samples is arranged in the form of a filter plate which allows chromatography by centrifugation (spin multiwell plate).

The material used for the chromatographic device can be a multiplicity of materials known from the prior art for such devices, such as, for example, glass, coated stainless steel, plastics, etc., without being restricted thereto. Preferably, the base body consists of a material containing an organic polymer preferably selected from the group consisting of polyethylene (PE) and polypropylene (PP), polycarbonate, polystyrene, polyphenysulfone or polysulfone. The device according to the invention is suitable for chromatographically isolating and/or purifying double-stranded nucleic acids from a mixture of such nucleic acids with single-stranded nucleic acids, oligonucleotides such as, for example, excess primers, mononucleotides such as dNTPs, salts and/or other contaminants which are typically present in nucleic acid-containing samples, more particularly in samples after PCR has been carried out. Preferably, the device according to the invention can be used for isolating and/or purifying PCR amplification products from the reaction mixture.

The present invention further provides a method for chromatographically isolating and/or purifying double-stranded nucleic acids from a mixture of such nucleic acids with single-stranded nucleic acids, oligonucleotides, mononucleotides, salts and/or other contaminants, preferably for isolating and/or purifying PCR amplification products from the reaction mixture, comprising the following steps: (1) providing a sample containing at least double-stranded nucleic acids in the form of an aqueous solution; (2) applying said solution to the inlet-facing side of the stationary phase of the chromatographic device according to the invention; (3) eluting the double-stranded nucleic acids and simultaneously collecting the eluate, with the separation of the double-stranded nucleic acids from the further constituents present in the sample being achieved in a single chromatographic step.

In contrast to the chromatographic methods used to date for purifying double-stranded nucleic acids, more particularly for purifying PCR amplification products from the reaction mixtures, the method according to the invention is a so-called "negative" chromatography, in which the molecule to be purified is not bound to/retained by the stationary phase, but rather the contaminants (single-stranded DNA, RNA, oligonucleotides such as primers, mononucleotides such as dNTPs, salts, etc.) interact with the stationary phase and are retained thereby, whereas the double-stranded DNA passes through the stationary phase together with the water present in the sample (the mobile phase). Therefore, in the context of the invention, the elution of double-stranded nucleic acids refers to the step of the method in which the double-stranded nucleic acids pass through the stationary phase in the solvent volume applied with the sample. Therefore, in the context of the invention, the term elution has to be distinguished from the so-called desorptive elution of the bind-wash-elute methods and also the fractionating elution of classic retention chromatography, in which a multiple of the column volume of an appropriate solvent is conducted across a stationary phase in order to obtain successively in particular fractions the particular substances of a substance mixture applied to the stationary phase. The chromatographic method according to the invention allows isolation and/or purification of double-stranded nucleic acids in a single chromatographic elution step.

Here, not only soluble contaminants can be removed, but the stationary phase of the device according to the invention also acts as a kind of filter for solid (undissolved) material, for example for precipitates or solid material which remains following cell lysis. They do not enter the stationary phase with the solution, but are retained on its surface. Another fact that should be highlighted is that the sample, after purification, has approximately the same volume and approximately the same concentration of double-stranded nucleic acids as before purification, without the need for additional steps for concentrating the eluate (for example, by precipitation, evaporation, etc.). As a result, potential sources of error, for example when transferring or pipetting, are avoided and losses in yield are minimized. Furthermore, specific buffers or other solutions for attachment and detachment of the substances to be purified are not required, making the method more cost-effective and faster than the methods typically used for the chromatography of double-stranded nucleic acids. This is clarified by FIG. 8, which shows the parallel purification of a multiplicity of samples in a multiwell plate using a bind-wash-elute method (left-hand column) and using the method according to the invention (right-hand column). Whereas the bind-wash-elute method requires at least three chromatographic steps, the isolation and purification in the method according to the invention is achieved in a single chromatographic step, preferably by centrifugation, symbolized by the curved arrow in FIG. 8.

Using the method according to the invention, it is possible to isolate and/or purify all types of double-stranded nucleic acids, such as double-stranded ribonucleic acids (RNA), in which both strands of the double strand are ribonucleic acids, double strands composed of, in each case, an RNA strand and a DNA strand, and double-stranded nucleic acids, in which both strands are deoxyribonucleic acids (DNA). The double-stranded nucleic acids are not restricted in terms of length and can, for example, be double strands composed of oligonucleotides having a relatively low number of nucleotide units, for example composed of 5 to 100 mononucleotides per strand, but also double strands of any desired number of bases, for example short to long-chain PCR products (typically 50 bp to several kb) up to plasmid DNA and genomic DNA (gDNA) (several kb up to the mega by range). Preferably, the double-stranded nucleic acids are double-stranded deoxyribonucleic acids (DNA), particularly preferably the linear double-stranded DNA of any desired length, for example 50 bp to 10 kb, obtained as PCR amplification products.

Preferably, the sample from which the double-stranded nucleic acids are isolated and/or purified using the method according to the invention is the reaction mixture obtained from a PCR without subsequent purification steps. Thus, after the PCR has ended, it is possible for the reaction mixture, without subsequent processing and/or purification steps such as dilution, extraction, precipitation or other methods typically used for processing and/or purification, to be added directly to the chromatographic device according to the invention and to be purified in a single chromatographic step using the method according to the invention, and in this case both single-stranded nucleic acids, more particularly ssDNA, and all low-molecular-weight constituents, for example salts and dNTPs, are removed as far as possible and the purified double-stranded DNA (the PCR product) is situated in the eluate. Here, it is especially advantageous that the dsDNA is present in virtually the same concentration as before purification and has not been diluted during chromatography. The method according to the invention thereby does not require additional steps for concentrating the sample from the eluate, but rather the eluate can be used directly after chromatography for subsequent assays or analyses.

The strength of noncovalent bonding between the immobilized metal ions and the nitrogen heterocycles of the mononucleotides and single-stranded nucleic acids is dependent, inter alia, on the pH of the sample solution. Advantageously, chromatographic purification is carried out at a pH of about 4 to 10. If necessary, the pH of a sample can be adjusted by addition of an appropriate buffer prior to application of the sample solution to the stationary phase of the chromatographic device according to the invention. Appropriate buffers are water-based buffers, comprising, for example, Good's buffers such as Mops, Mes and Hepes and also aqueous saline solutions, for example of alkali metal acetates or phosphates. Substances having a high affinity for metal ions, for example tricine or citrate, are preferably avoided as buffer constituents. For adjustment of the pH suitable for chromatographic purification, the reaction mixture obtained from the PCR is preferably admixed with 1/20 to 1/30 of its volume of said buffer solution and subsequently added to the stationary phase of the chromatographic device.

Preferably, the method subsequently additionally comprises a step involving incubation of the solution applied to the stationary phase prior to elution of the double-stranded nucleic acids. The incubation, which may preferably be carried out by simply allowing the sample solution-loaded device to stand at room temperature, further improves the selective binding of the single-stranded nucleic acids and mononucleotides to the immobilized metal ions. Neither the temperature nor the incubation time is subject to any particular restrictions, and the incubation can, for example, be carried out at from 0° C. to 80° C. over a period of from a few seconds up to several hours. Preferably, the incubation is at room temperature over a period of from 0 seconds to 20 minutes, preferably from 10 seconds to 10 minutes, more preferably from 15 seconds to 5 minutes, especially preferably from 30 seconds to 2 minutes and very particularly preferably 1 minute.

The method according to the invention is notable, inter alia, for the fact that the volume of the eluate obtained is comparable to the volume of the sample solution applied to the stationary phase. Preferably, the volume of the eluate obtained after the chromatographic purification deviates by no more than +/−50%, preferably +/−20%, from the volume of the sample solution applied to the stationary phase.

The stationary phase in the chromatographic device is created by filling a suspension of the chromatography resin or of the chromatography resin and the further material. Preferably, a suspension having an about 30-70%, for example about 50%, solids content of the (swollen) resin and/or of the further material is filled into (the) at least one cavity of the base body for example. Since the suspension is a swollen resin, this corresponds to a solids content in the suspension of about 3 to 10%, preferably about 5 to 7%. When using a customary spin column which fits into a 1.5 ml Eppendorf tube as a chromatographic device, the total weight of suspension consists of about 600 to 700 mg, corresponding to approximately 600 to 700 μg of suspension.

The sample containing the double-stranded nucleic acids to be isolated and/or purified is added as an aqueous solution (mobile phase) to the surface of the stationary phase and then passes through the stationary phase (elution) because of gravity or by application of positive or negative pressure or by the action of centrifugal forces, without being restricted thereto. For the elution of the double-stranded nucleic acids, it is not required to add additional solvent apart from the volume contained in the applied sample. Preferably, the double-stranded nucleic acids are eluted by application of centrifugal force to the chromatographic device. In this case, the chromatographic device is preferably in the form of a suitably sized spin column or of a filter plate which can be inserted into a centrifuge. Preferably, to this end, the chromatographic device is centrifuged for from 1 second to 20 minutes, particularly preferably from 10 seconds to 10 minutes, and more particularly from 30 seconds to 1 minute. The applied centrifugal force is preferably from 30 to 3000 g, particularly preferably from 300 to 2000 g, and more particularly 750 g.

The chromatographic device according to the invention can, on the one hand, be in the form of a prepacked chromatographic device in which the stationary phase is already present in the cavity of the chromatographic device as a suspension in an appropriate solvent, preferably as a suspension in an aqueous buffer, which is removed to form the chromatography-suitable matrix prior to application of the sample to be purified by gravity, positive or negative pressure and preferably by application of centrifugal force.

Alternatively, the stationary phase can also be contained in the chromatographic device in a dry state or the chromatographic materials forming the stationary phase can be provided separately from the chromatographic device. In this case, the method according to the invention additionally comprises a step for preparing the gel matrix by suspending the chromatographic materials in water, an aqueous solution or an aqueous buffer, allowing the materials to swell in the suspension to form the gel matrix, and removing the excess water, aqueous solvent or aqueous buffer by centrifugation of the chromatographic device containing the swollen resin prior to application of the sample solution to the stationary phase. Here, the chromatography resin can be filled into the chromatographic device before or after allowing it to swell by means of water, an aqueous solution or an aqueous buffer.

The invention further comprises a kit for isolating and/or purifying double-stranded nucleic acids, preferably double-stranded DNA, comprising the chromatographic device according to the invention or the starting materials thereof, for preparing the chromatographic device for use in accordance with the previous paragraph, and optionally a buffer solution for adjusting the pH of the sample solution prior to chromatographic purification. The buffer solution is preferably selected from the group containing Mops, Mes, Hepes and aqueous solutions of alkali metal acetates or phosphates, and is particularly preferably an aqueous sodium acetate solution.

EXAMPLES

Example 1

Preparing a Spin Column According to the Invention

About 7 g of solid Sephadex G50 (GE Healthcare, Munich, Germany) were swollen for several hours in 100 mg of $dH_2O$ or 0.02% sodium azide solution (about 7% w/v or about 50% v/v), and filled into a commercially available filtration column containing a frit (Qiagen, Hilden, Germany) and overlaid with 300 μl of 50% (v/v) $Cu^{2+}/Al^{3+}$ IDA agarose (IDA Superflow 6 suspension (QIAGEN, Hilden, Germany) was mixed with an excess of a 250 mM solution of the corresponding ions and shaken overnight at room temperature; thereafter, washing was carried out ten times with $dH_2O$ and the suspension was adjusted to 50% v/v in the appropriate binding buffer). As a result of centrifugation at 1000 g for 5 min, the excess solvent used for swelling was removed and the gel matrix prepared for chromatography.

Example 2

Purification of Double-Stranded Nucleic Acids from a PCR Mixture

25 μl of the reaction mixture obtained from a PCR were admixed with 1 μl of 3 M NaAc (aqueous, pH 5.5) and added to the inlet-facing side of the stationary phase of a spin column described in example 1. The loaded column was allowed to stand at room temperature for 1 min and subsequently centrifuged at 1000 g for 5 min, with collection of the eluate in a suitable collection tube. The elution volume was comparable to the starting sample volume of about 25 µl.

Example 3

Removal of Excess dNTPs and Primers

To illustrate the purification effect of the chromatographic devices according to the invention, 25 µl of a PCR-obtained reaction mixture were admixed with 30 µmol of dNTPs (final concentration) or 100 pmol of reverse primers and subsequently purified using a commercially available Sephadex spin column (QIAGEN, Hilden, Germany) or the chromatographic device according to the invention as described in example 2. The eluates obtained were subsequently analyzed in each case by sequencing. The results are shown in FIGS. 6a to 7b.

Figure 1:
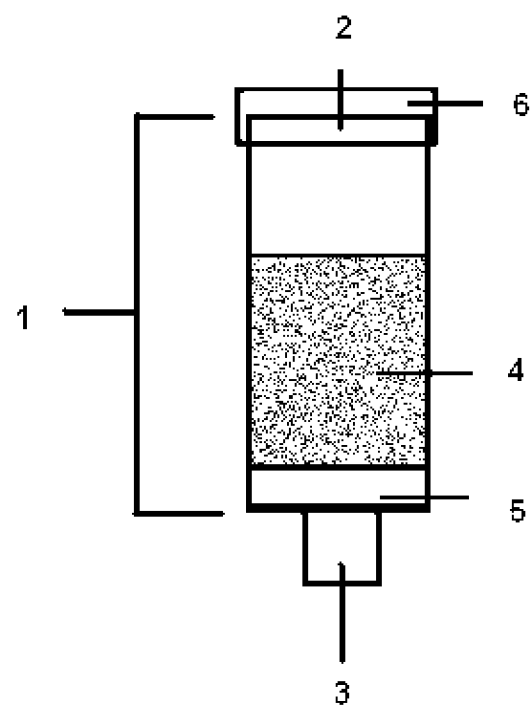
FIG. 1 is a diagram showing the chromatographic device according to the invention comprising a base body (1) which defines, within its interior, a cavity in which a stationary phase (4) is situated and which is additionally provided with an inlet (2), an outlet (3) and a porous frit (5) which retains the stationary phase in the cavity, and also a lid (6) as a closure device for closing the inlet (2) of the cavity.
Figure 2:
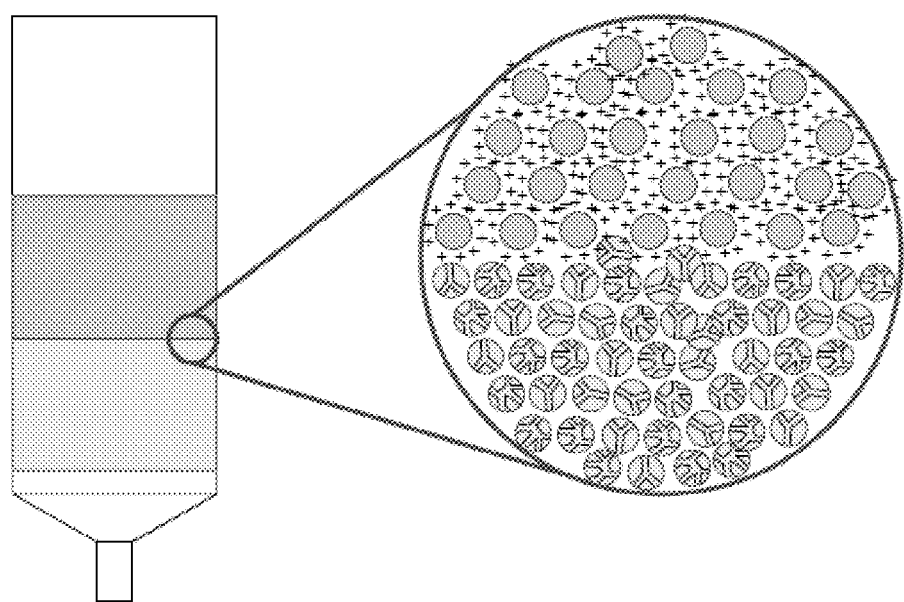
FIG. 2 shows a preferred embodiment of the stationary phase present in the cavity, in which phase the material on which the metal ions are immobilized and the porous size-exclusion chromatography resin are arranged in the form of two successive, separate layers in the flow direction of the mobile phase from the inlet to the outlet. In this figure, the upper layer in the flow direction is the chromatographic material on which the metal ions are immobilized. It is depicted in FIG. 2 as beads surrounded by positive charges (symbolized by "+"). The porous size-exclusion chromatography resin is arranged here in the flow direction as the lower layer and depicted as beads having internal channels.
Figure 3:
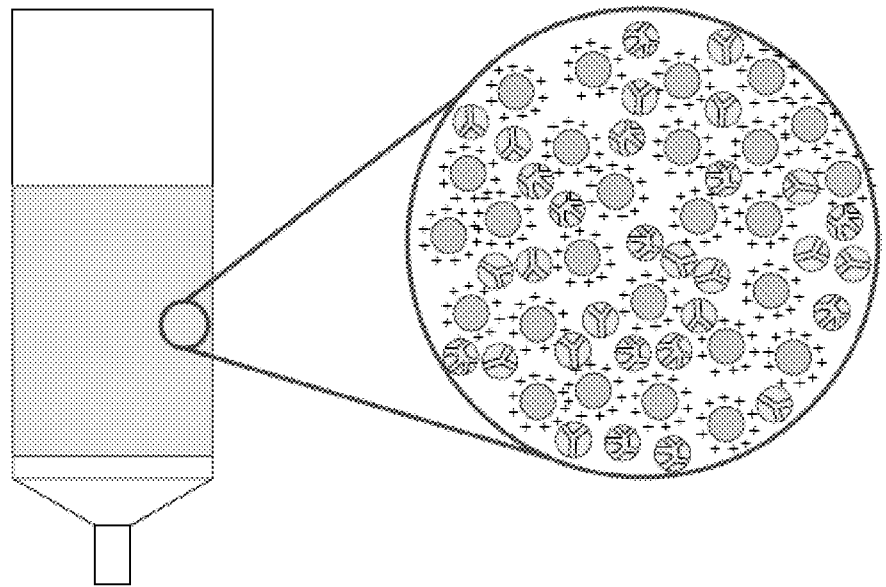
FIG. 3 shows a further preferred embodiment of the stationary phase of the chromatographic device according to the invention, in which the stationary phase is present as a largely homogeneous mixture (so-called mixed-bed resin). The symbolic depiction of the different chromatography media is as explained in FIG. 2.
Figure 4:
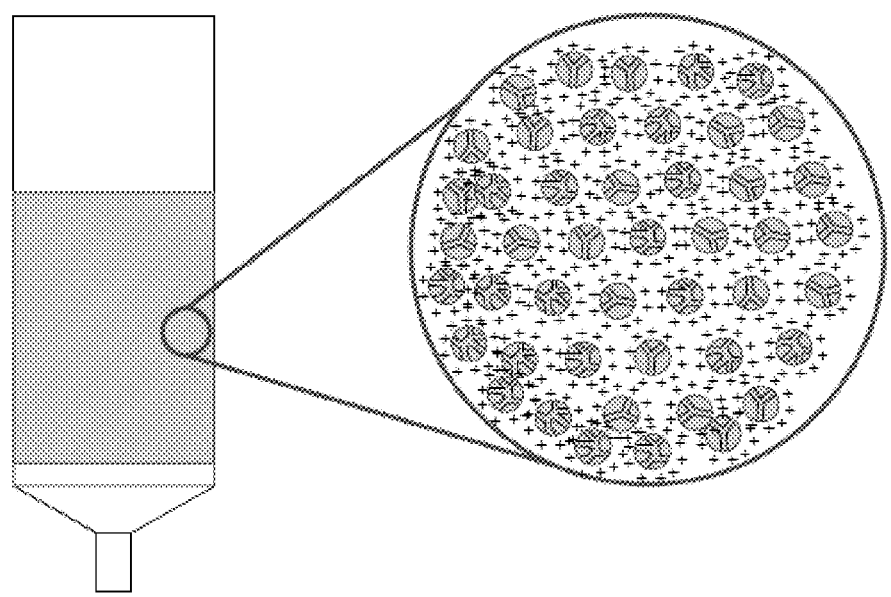
FIG. 4 shows a further preferred embodiment of the stationary phase of the chromatographic device according to the invention, in which the metal ions are themselves immobilized on the size-exclusion chromatography resin, illustrated by the positive charges surrounding the beads having internal channels.
Figure 5:
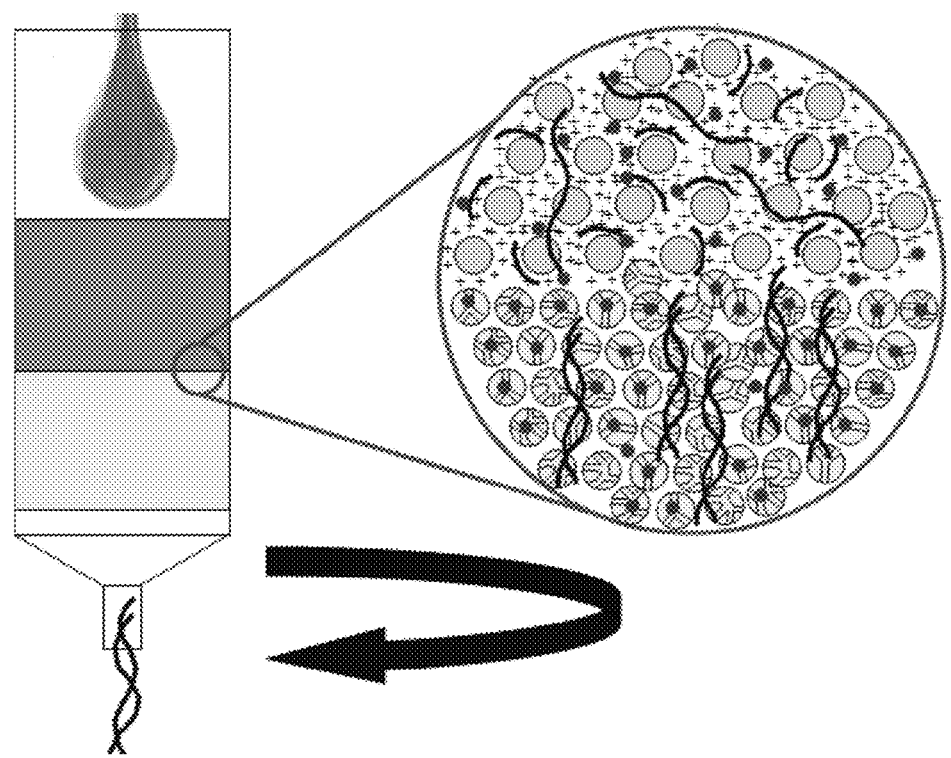
FIG. 5 is a diagram showing chromatographic purification using the device according to the invention. In the embodiment shown, the porous size-exclusion chromatography resin and the material containing the immobilized metal ions are arranged in two separate layers. Upon centrifugation (symbolized by the curved arrow), the applied sample passes first through the material on which the metal ions are immobilized. Here, as a result of noncovalent interactions, single-stranded nucleic acids (symbolized by individual black wavy lines) and dNTPs are retained on said material, whereas the double-stranded nucleic acids (depicted by, in each case, two entwined black wavy lines) and other contaminants such as salts (depicted by small, filled circles) can pass through this first chromatographic layer. Immediately following this first layer is the second chromatographic layer, which is formed by the porous size-exclusion chromatography resin. Low-molecular-weight constituents such as salts enter into the pores of the size-exclusion chromatography resin and are retained therein, whereas the double-stranded nucleic acids are not able to enter into the pores owing to their size or their hydrodynamic volume and thus emerge with the desalted solvent from the outlet of the chromatographic device in purified form.
Figure 6A:
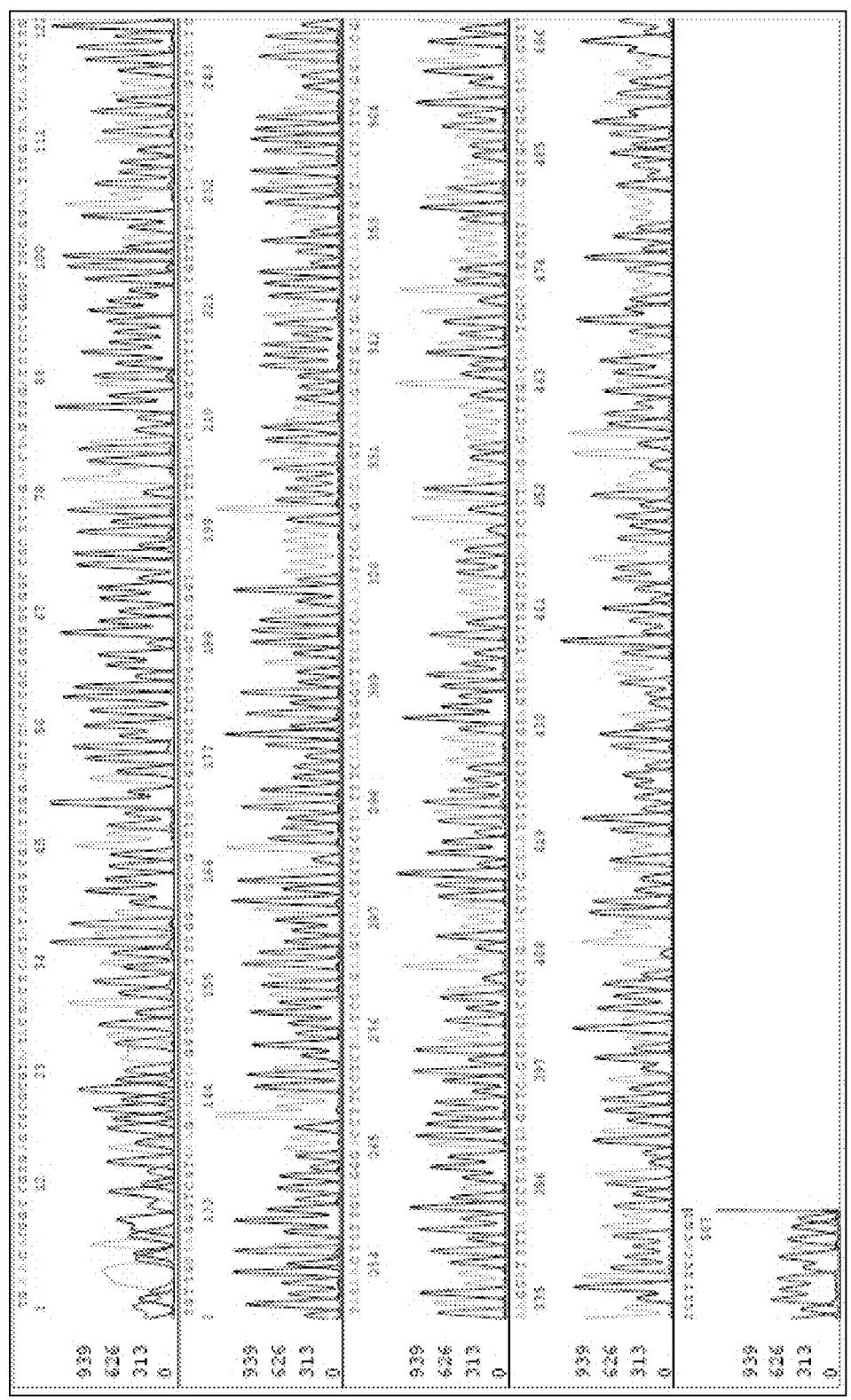
FIGS. 6a and 6b show the sequencing result of a PCR-obtained reaction mixture which was admixed with 30 μmol dNTPs prior to purification and subsequently purified across a Sephadex spin column (FIG. 6a) or across a spin column according to the invention containing a combination of a Sephadex material and immobilized $Cu^{2+}$ and $Al^{3+}$ ions (FIG. 6b).
Figure 6B:
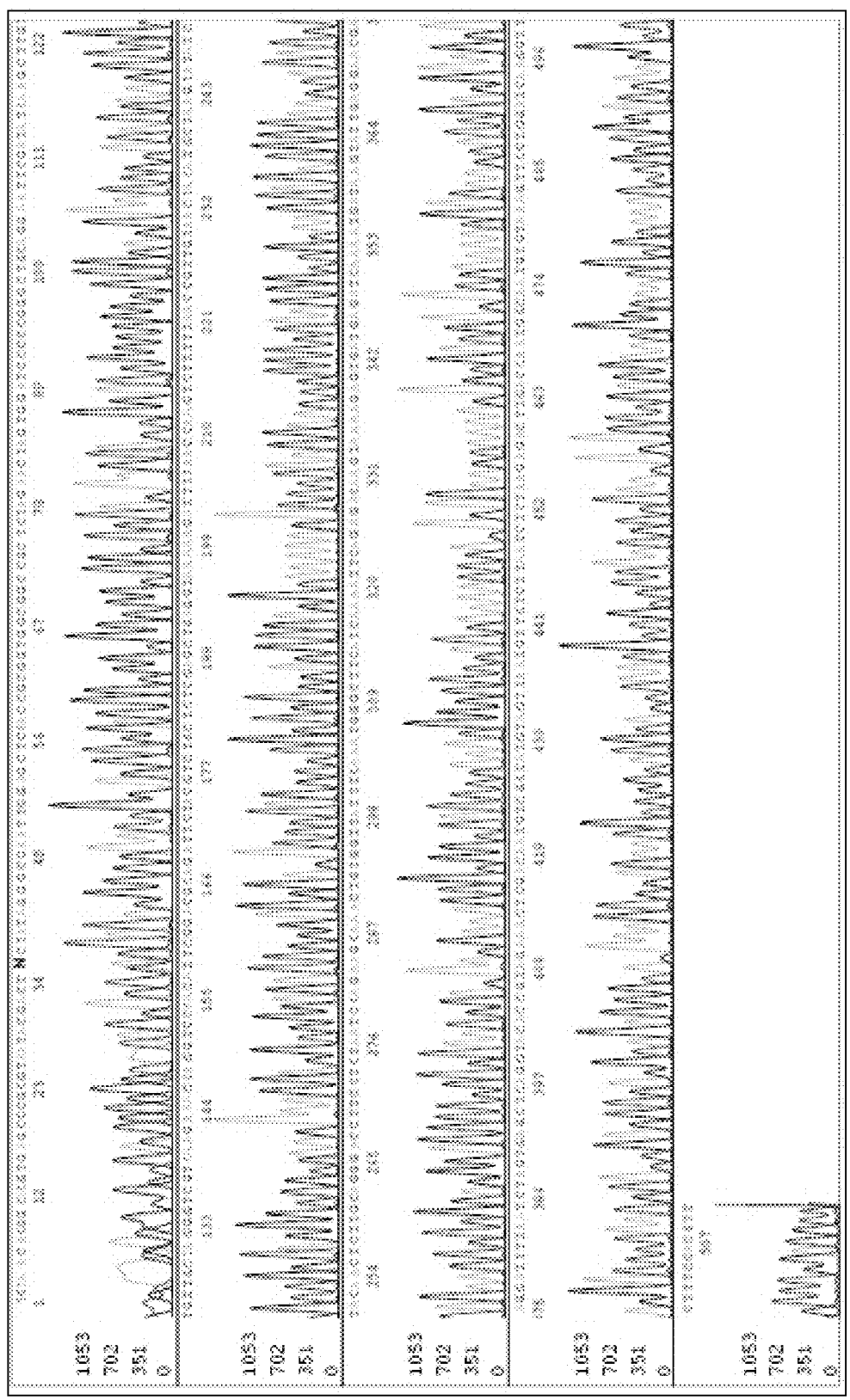

It can be clearly seen from FIGS. 6a (purification using Sephadex) and 6b (purification using the device according to the invention) that the electropherogram of that sample purified using the device according to the invention is notable for distinctly sharper signals (peaks) and little to no background noise. Compared to the sample purified using the commercially available Sephadex column, the sample purified using the device according to the invention is of distinctly higher quality according to the electropherogram, showing that even a large excess of nonincorporated dNTPs can be effectively removed using the device according to the invention.

Figure 7A:
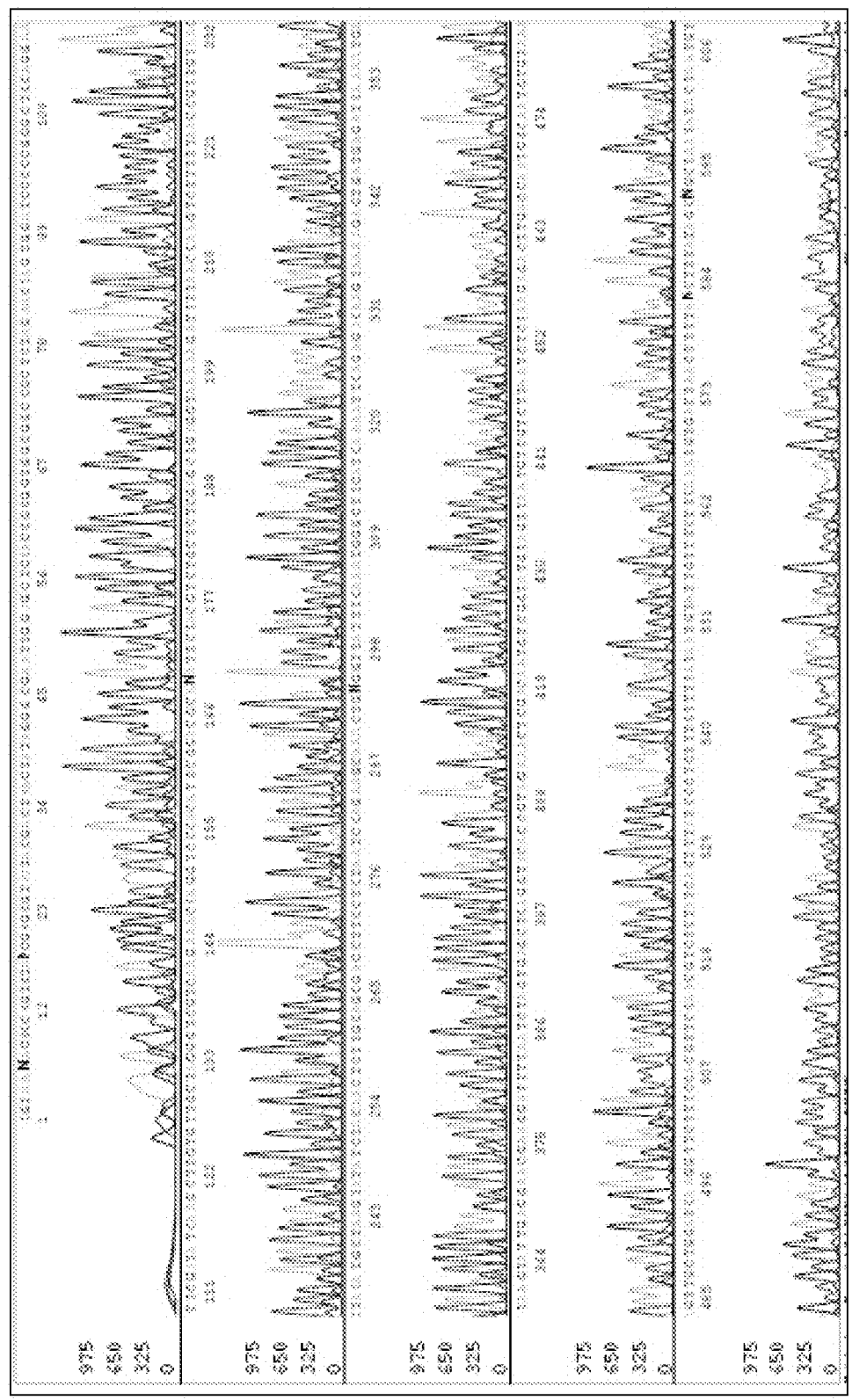
FIGS. 7a and 7b show the sequencing result of a PCR-obtained reaction mixture which was admixed with 100 pmol of reverse primers prior to purification and subsequently purified across a Sephadex spin column (FIG. 7a) or across a spin column according to the invention containing a combination of a Sephadex material and immobilized $Cu^{2+}$ and $Al^{3+}$ ions (FIG. 7b).
Figure 7B:
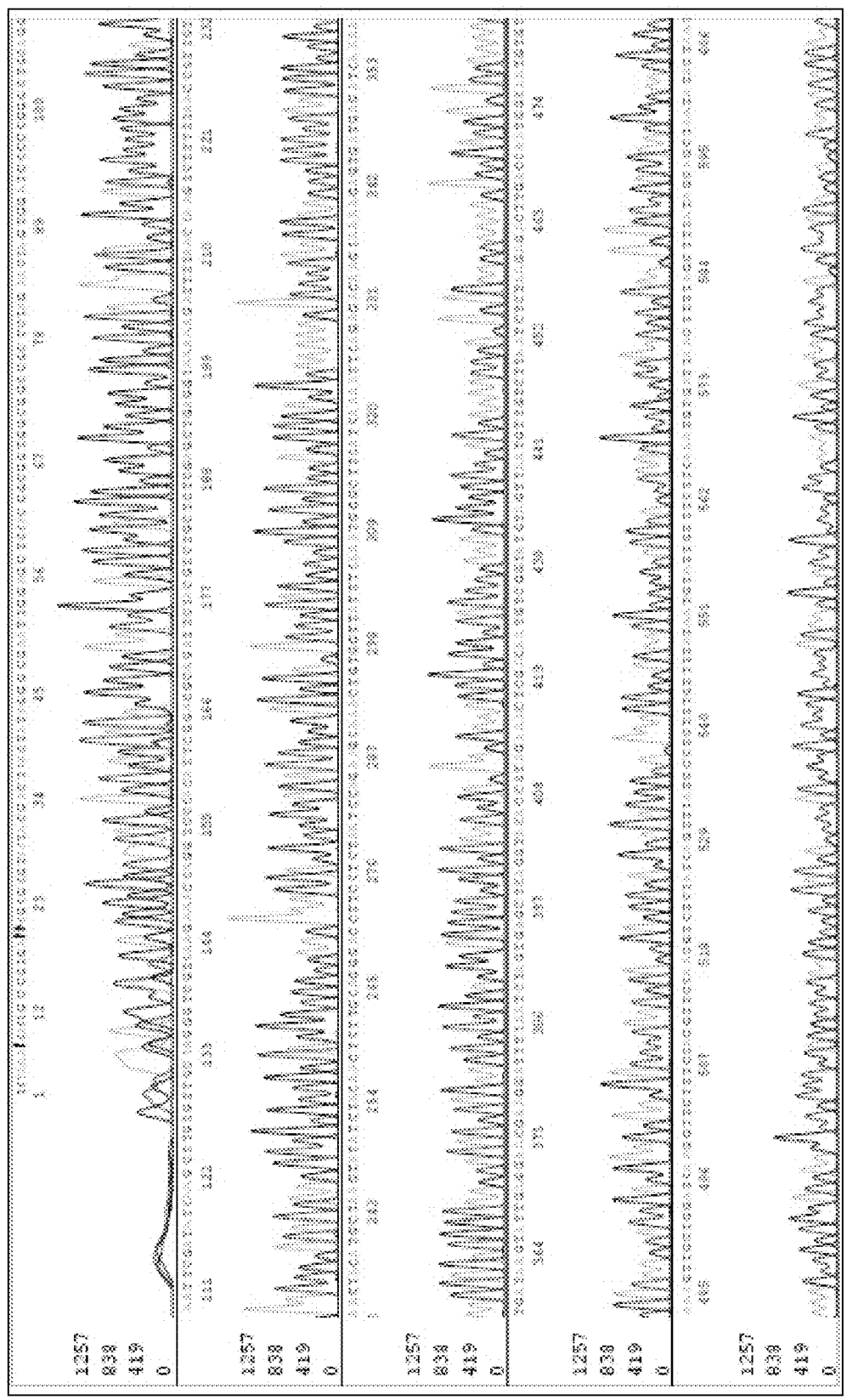
Figure 8:
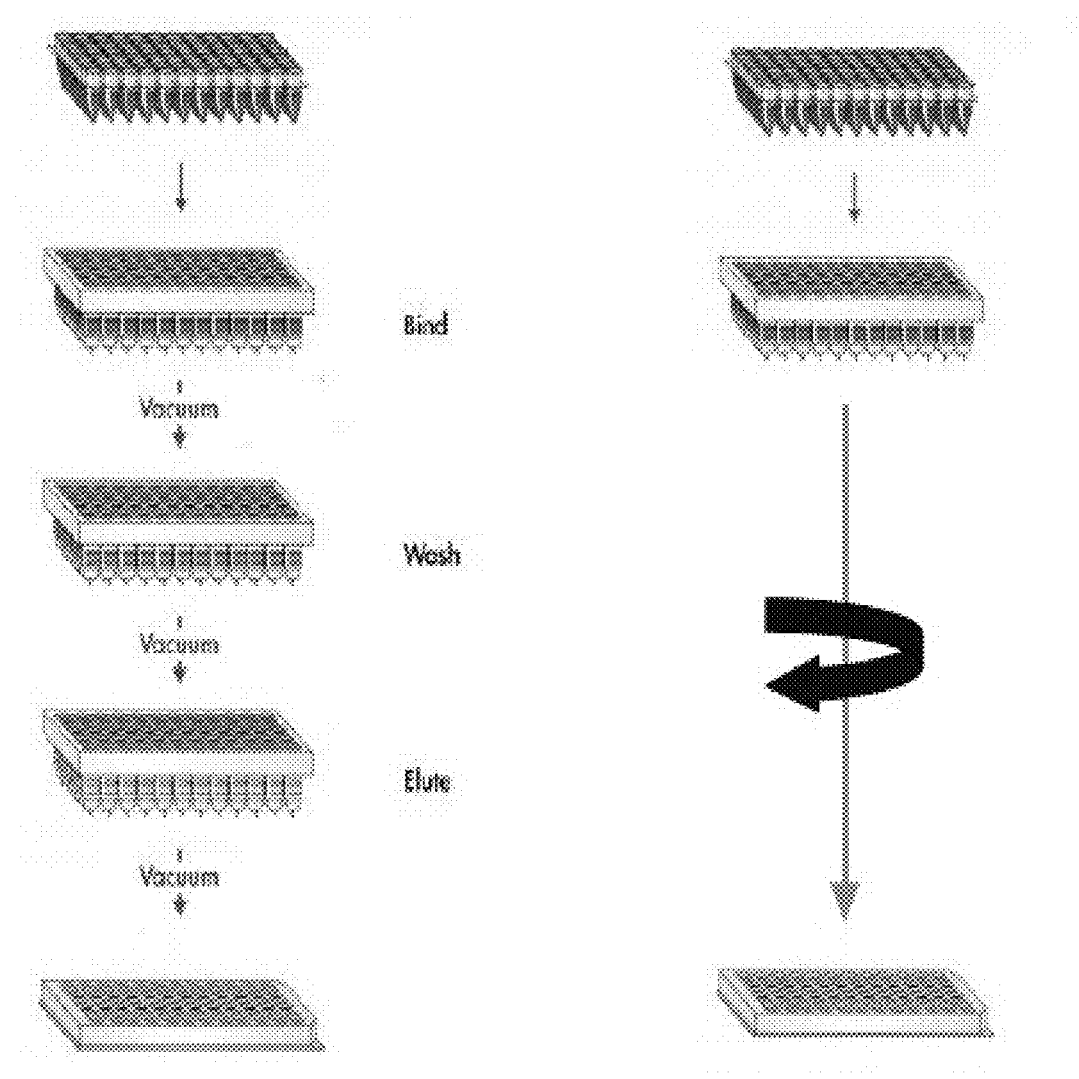
FIG. 8 shows a comparison of the necessary steps when chromatographically purifying nucleic acid-containing samples using a) adsorption materials requiring a so-called bind-wash-elute routine (left-hand side) and b) a chromatographic device according to the invention in the form of a so-called spin multiwell plate.

The same trend can be seen in FIGS. 7a and 7b, which show the electropherogram of a sequencing reaction of two PCR samples, of which one was purified using a commercially available Sephadex spin column (FIG. 7a) and the other using the device according to the invention (FIG. 7b), after both were admixed beforehand with, in each case, 100 pmol of reverse primers.

The invention claimed is:

1. A chromatographic device for isolating and/or purifying double-stranded nucleic acids, comprising:
   (1) a base body,
   (2) at least one cavity within the base body, which cavity is provided with an inlet and an outlet, and
   (3) a stationary phase situated in the cavity, wherein the stationary phase comprises:
      (a) a size-exclusion chromatography medium for isolating and/or purifying double-stranded nucleic acids, wherein the size-exclusion chromatography medium comprises at least one porous chromatography resin having pores sufficiently small to disallow a double-stranded nucleic acid of more than 100 bp to enter, and
      (b) immobilized metal ions, and
   (4) a porous filter, a porous frit or a membrane that is arranged between the outlet of the cavity and the stationary phase and retains the stationary phase in the cavity.

2. The device of claim 1, wherein the double-stranded nucleic acids are double-stranded DNA.

3. The device of claim 1, further comprising at least one of the following features: at least one closure device for closing the inlet and/or the outlet of the cavity and at least one collection vessel for collecting the mobile phase (eluate) emerging from the outlet after elution has occurred.

4. The device of claim 1, wherein the immobilized metal ions are divalent, trivalent or tetravalent metal cations or mixtures thereof.

5. The device of claim 4, wherein the immobilized metal ions are selected from the group consisting of $Zn^{2+}$, $Co^{2+}$, $Cu^{2+}$, $Ni^{2+}$, $Fe^{2+}$, $Mn^{2+}$, $Al^{3+}$, $Co^{3+}$, $Ga^{3+}$ and $Zr^{4+}$, and a combination thereof.

6. The device of claim 4, wherein the immobilized metal ions are at least one divalent metal cation selected from the group consisting of $Zn^{2+}$, $CO^{2+}$, $Cu^{2+}$ and $Ni^{2+}$, optionally in combination with $Al^{3+}$ ions.

7. The device of claim 4, wherein the immobilized metal ions are $Cu^{2+}$ ions, optionally in combination with $Al^{3+}$ ions.

8. The device of claim 1, wherein the metal ions are immobilized on at least part of the stationary phase by means of at least one linker.

9. The device of claim 8, wherein the linker has the general formula A-R—Z, where A is an anchor group for covalent bonding of the linker to at least part of the stationary phase, Z is a polydentate head group for chelating the metal ions, and R is a linear, branched or cyclic hydrocarbon chain that connects the anchor group A and the head group Z, that can be substituted or unsubstituted, and in which one or more carbon atoms can be replaced by heteroatoms.

10. The device of claim 8, wherein the linker is selected from the group consisting of iminodiacetic acid (IDA), nitrilotriacetic acid (NTA), N-carboxymethylated aspartic acid (CM-Asp), and tris(2-ethylaminoethyl)amine (TREN).

11. The device of claim 1, wherein the porous chromatography resin is a crosslinked silicate or an organic polymer that, upon mixing with water, an aqueous solution or an aqueous buffer, forms a gel matrix having internal pores of a defined size (size-exclusion chromatography resin).

12. The device of claim 11, wherein the porous chromatography resin is selected from the group consisting of dextrans, agarose, polyacrylamides, and mixtures thereof.

13. The device of claim 1, wherein the stationary phase comprises, in addition to the at least one porous chromatography resin (size-exclusion chromatography resin), at least one additional material on which the metal ions are immobilized.

14. The device of claim 13, wherein the porous chromatography resin and the additional material in the chromatographic device
   a) are arranged substantially separately from one another, or
   b) are largely present as a homogeneous mixture.

15. The device of claim 14, wherein the porous chromatography resin and the additional material in the chromatographic device are arranged substantially separately from one another in the form of two successive layers in the flow direction of the mobile phase from the inlet to the outlet.

16. The device of claim 15, wherein the additional material is arranged as the upper layer, and the size-exclusion chromatography resin is arranged as the lower layer.

17. The device of claim 1, wherein the metal ions are immobilized on the porous chromatography resin.

18. The device of claim 1, wherein the chromatographic device
   i) comprises exactly one stationary phase-filled cavity, or
   ii) comprises, for the parallel isolation and/or purification of double-stranded nucleic acids from different samples, multiple cavities that are each filled with the stationary phase and are arranged in parallel.

19. The device of claim 18, wherein the chromatographic device is in the form of a spin column.

20. The device of claim 18, wherein the multiple cavities are arranged in the form of a filter plate.

21. The device of claim 1, wherein the base body consists of a material containing an organic polymer.

22. The device of claim 21, wherein the organic polymer is selected from the group consisting of polyethylene (PE), polypropylene (PP), polycarbonate, polystyrene, polyphenylsulfone, and polysulfone.

23. A method for chromatographically isolating and/or purifying double-stranded nucleic acids from a mixture of such nucleic acids with single-stranded nucleic acids, oligonucleotides, mononucleotides, salts and/or other contaminants, comprising:
   (1) providing a sample containing at least double-stranded nucleic acids in the form of an aqueous solution,
   (2) applying said solution to the inlet-facing side of the stationary phase of a chromatographic device of claim 1, and
   (3) eluting the double-stranded nucleic acids and simultaneously collecting the eluate,
   wherein the separation of the double-stranded nucleic acids from the further constituents present in the sample is achieved in one chromatographic step.

24. The method of claim 23, wherein the method is for isolating and/or purifying PCR amplification products from a PCR reaction mixture.

25. The method of claim 23, wherein the double-stranded nucleic acids are double-stranded deoxyribonucleic acids (DNA).

26. The method of claim 23, wherein the double-stranded nucleic acids are linear double-stranded DNA obtained as PCR amplification products.

27. The method of claim 23, wherein the double-stranded nucleic acids are eluted by application of centrifugal force to the chromatographic device.

28. The method of claim 27, additionally comprising:
preparing a gel matrix in the cavity of the chromatographic device by suspending a porous chromatography resin in water, an aqueous solution or an aqueous buffer, allowing the resin to swell in the suspension to form the gel matrix, and removing the excess water, aqueous solvent or aqueous buffer by centrifugation of the chromatographic device containing the swollen resin prior to step (2).

29. A kit for isolating and/or purifying double-stranded nucleic acids, comprising a chromatographic device of claim 1 or the starting materials thereof and optionally a buffer solution for adjusting the pH of the sample solution prior to chromatographic purification.

30. The kit of claim 29, wherein the double-stranded nucleic acids are double-stranded DNA.

31. The kit of claim 29, wherein the buffer solution is selected from the group containing Mops, Mes, Hepes and aqueous solutions of alkali metal acetates or phosphates.

32. The kit of claim 31, wherein the buffer solution is an aqueous sodium acetate solution.

33. The device of claim 1, wherein the at least one porous chromatography resin has pores sufficiently small to disallow a molecule having a molecular weight larger than 10,000 daltons to enter.

34. The device of claim 1, wherein the at least one porous chromatography resin has pores sufficiently small to disallow a double-stranded nucleic acid of more than 80 bp to enter.

35. The device of claim 1, wherein the at least one porous chromatography resin has pores that allow a molecule having a molecular weight below 10,000 daltons to enter.

36. The device of claim 1, wherein the at least one porous chromatography resin has pores that allow a molecule having a molecular weight below 1,000 daltons to enter.

* * * * *